United States Patent [19]
Thompson et al.

[11] Patent Number: 4,983,849
[45] Date of Patent: Jan. 8, 1991

[54] APPARATUS AND METHOD FOR PROMOTING UNIFORM DOSAGE OF IONIZING RADIATION IN TARGETS

[75] Inventors: Chester C. Thompson, Rosyln Heights; Marshall R. Cleland, Hauppauge; Edward J. Lopez, Stony Brook, all of N.Y.

[73] Assignee: Radiation Dynamics, Inc., Edgewood, N.Y.

[21] Appl. No.: 361,323

[22] Filed: Jun. 5, 1989

[51] Int. Cl.⁵ .............................................. H01J 37/04
[52] U.S. Cl. ................................ 250/492.3; 250/505.1
[58] Field of Search ............... 250/492.1, 492.3, 503.1, 250/505.1; 313/310

[56] References Cited

U.S. PATENT DOCUMENTS

| | | | |
|---|---|---|---|
| 2,814,727 | 11/1957 | Gund et al. | 250/492.3 |
| 2,825,486 | 10/1957 | Zoubek . | |
| 2,858,441 | 10/1958 | Gale . | |
| 3,081,485 | 3/1963 | Steigerwald . | |
| 3,440,466 | 4/1969 | Colvin et al. | 250/492.3 |
| 3,535,205 | 10/1970 | Bate . | |
| 3,702,412 | 11/1972 | Quintal | 313/420 |
| 3,942,071 | 8/1974 | Uehara | 250/492.3 |
| 4,178,220 | 2/1979 | Fowler . | |
| 4,324,980 | 4/1982 | Symmons | 250/505.1 |
| 4,652,763 | 3/1987 | Nablo | 250/492.3 |
| 4,734,586 | 3/1988 | Crist et al. | 250/492.3 |

OTHER PUBLICATIONS

A. M. Koehler, R. J. Schneider and J. M. Sisterson, *Nuclear Instruments and Methods*, "Range modulators for Protons and Heavy Ions", North Holland Publishing Co.

Primary Examiner—Bruce C. Anderson
Attorney, Agent, or Firm—Howard L. Rose

[57] ABSTRACT

Apparatus and method for attenuating the energy and increasing the angular scattering of a radiation beam particularly suited for electron beams and for promoting dose uniformity in irradiated target products, including using a cooled, intermediate scatter plate which may or may not be perforated and a radiation reflective target basket.

18 Claims, 4 Drawing Sheets

APPARATUS AND METHOD FOR PROMOTING UNIFORM DOSAGE OF IONIZING RADIATION IN TARGETS

TECHNICAL FIELD

This invention relates to apparatus and methods for modification of beams of ionizing radiation and promotion of dosage uniformity in irradiated targets. More particularly, this invention relates to the structure and use of cooled intermediate scatter plates with radiation beams.

BACKGROUND OF THE INVENTION

Ionizing radiation and especially electron beam accelerators are now employed in a multitude of industrial processes. Crosslinking of polymeric articles and sterilization of medical devices are common place. The use of electron beam accelerators in the sterilization of products such as syringes, surgical gloves, solution bottles, in the medical field is now becoming popular. The popularity corresponds to long-accepted crosslinking applications in the heat shrink cable connector field.

In electron beam sterilization processing, typically, target items will be packaged in a cardboard box type container, a plastic bag or distributed on a flat tray when subject to the beam. The product containing carrier is then placed on a conveyer or appropriate transport means, such as that depicted in U.S. Pat. 4,561,358, and passed through an electron beam chamber. Depending on the particular requirements of the target, the carrier may be subject to dual (multiple) simultaneous source exposure or multiple passes past a single source. These procedures ensure substantially complete, if not uniformly, irradiated articles.

Uniformity problems are often experienced in the processing of non-homogeneous target products, especially in the context of sterilization or irregularly shaped medical products. It is elementary, in the context of sterilization of medical products, that the irradiation procedures must effectively sterilize the entire target but must not adversely affect product functionality. Hence, at the optimal dose, the product is sterilized but is not discolored or degraded in its physical properties. In practice, however, irregularly shaped objects and especially those composed of non-homogeneous material, often present difficulties in achieving uniform irradiation dosage.

Dose uniformity in homogeneous products is represented graphically by a relatively smooth depth-dose distribution curve. Non-homogeneous, or non-uniform products do not lend themselves to such elementary analysis. The problem is particularly acute when a non-homogeneous target is composed of a non-homogeneous material. In such cases the dose (absorbed energy per unit mass) variation within a product can range from a fraction to many times that of the average dose.

There are a number of identifiable factors, independent of the target characteristics, which contribute to the effective dose at a particular location of a product. For example, as a radiation beam is scanned, target portions near the end of the scan present a greater apparent thickness to the beam. The apparent thickness is easily quantified by dividing the product thickness by the cosine of the angle of incidence. As the angle departs from normal incidence, the surface dose increases from enhanced back scattering within the irradiated product, itself. Also, it is elementary that as the (apparent) thickness increases, the effective dose at the back surface of the product is reduced.

Another significant contribution to dose variation, particularly acute in non-homogeneous products, is radiation scattering. When an electron beam enters a product, primary and secondary electrons will scatter at various angles and energies. Since there are fewer primary electrons at the beam scan ends than at the scan center, there are correspondingly far less secondary electrons distributed throughout the thickness of the target. If controlled, electron scatter can be employed to offset the unequal primary dose and can be utilized to promote uniform secondary electron density throughout the product.

One final example of dose contribution is the normal variation at different product depth, itself. Even in a homogeneous product, dose is dependent on the radiation penetration characteristics.

SUMMARY OF THE INVENTION

It is the object of the present invention to provide method and apparatus to overcome the problems of non-uniform dose distribution particularly in non-homogeneous products upon exposure of such products to ionizing radiation.

Another object of this invention is to provide method and apparatus operative to provide dose attenuation of a beam of ionizing radiation.

A further object of this invention is to provide method and apparatus operative to promote effective utilization of a scanning electron beam for high or low energy radiation treatment of non-homogeneous, irregularly shaped products.

Still another object of this invention is to provide means and a method for effectively sterilizing an entire, non-uniform, even irregularly-shaped target product in a non-damaging, non-destructive manner.

A further object of this invention is to minimize the differential dose distribution in non-homogeneous products resulting from conventional electron beam irradiation.

These and other objects are satisfied by an apparatus for promoting radiation dose uniformity in exposed targets. The apparatus comprises a source of ionizing radiation where the source includes means for generating a beam of ionizing radiation, and a beam source exit window. The target is located on target support means for supporting the target. The target support means is located at a selected distance from said window. The apparatus includes a mass means for absorbing energy of the radiation beam and which induces increased radiation scattering (angular dispersion). The mass means is located between said window and said target support means is cooled by a cooling means.

Still other objects are satisfied by a method of promoting dosage uniformity in targets exposed to beams of ionizing radiation issuing from an accelerator window, where the method includes the steps of, (1) adjusting the radiation energy level to at least achieve an equal entrance and exit dose level for the average thickness and density of the target, (2) positioning a scatter plate between the target and the accelerator window to absorb a portion of the beam energy and to induce radiation scatter, and (3) cooling the scatter plate.

A first general aspect of this invention is the control of the energy level of the radiation beam at a level greater than that necessary to achieve an equal entrance and exit for the average product density of the target product. Thus, low dose areas in the product are effectively minimized. An intermediate scatter plate is positioned between the target and beam source to, first, absorb some of the electron energy, and secondly, to induce scattering of the electrons. The intermediate plate increases the surface dose thereby reducing the disparity of the surface target dose and the maximum target dose. The plate substantially increases the number of scattered electrons as well as inducing a significantly greater scatter angle than the mere passage of the beam through a scan horn window. The thickness of the plate which determines the amount of scatter, is selected based on the particular requirements of the process (i.e. sterilization) and the products (i.e. syringes).

The invention also contemplates the use of a radiation reflective basket in which the target products are subjected to reflected radiation.

The benefit of the invention in high power industrial applications (4.5 MeV) context involves, among other aspects, increasing scatter and, consequently, dose at the periphery of the product container. For this reason, angled side scatter plates positioned along all four sides and, if necessary, on the bottom of the product container will further enhance peripheral dose uniformity by reflecting scattered electrons into the target.

DETAILED DESCRIPTION OF THE ILLUSTRATED EMBODIMENTS

Figure 1:
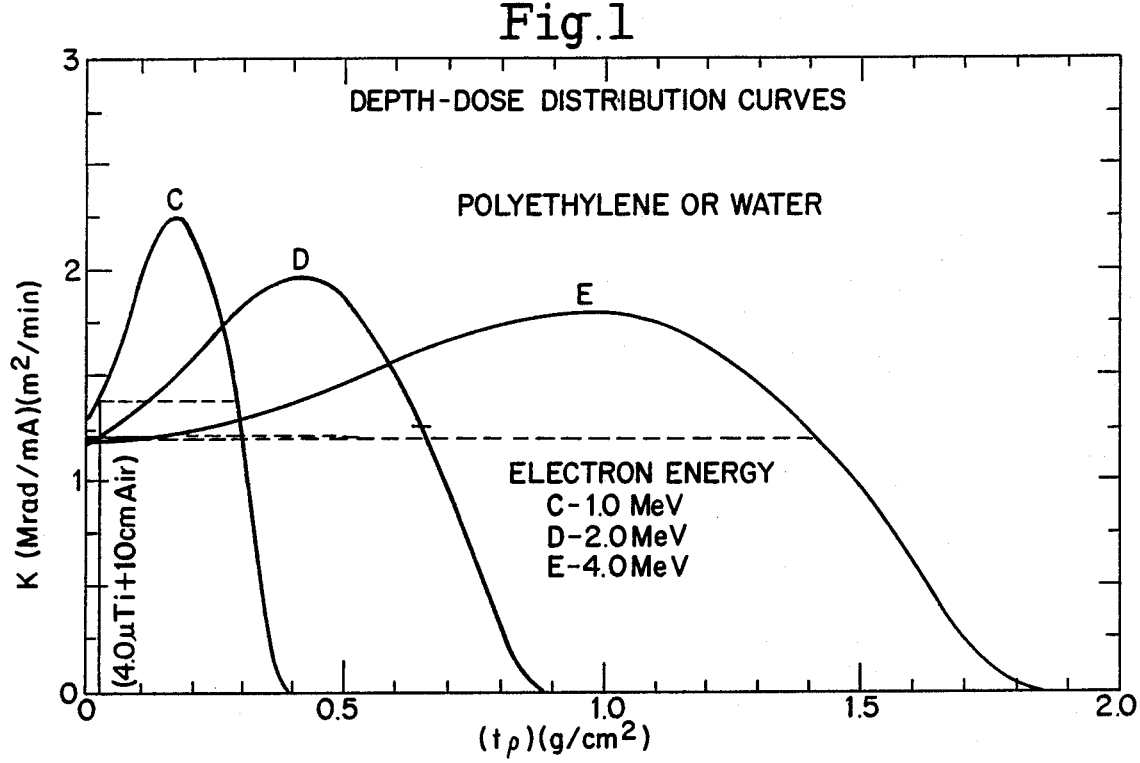
FIG. 1 is a depth dose distribution curve for polyethylene or water.

FIG. 1 is a depth-dose distribution curve representative of homogeneous products such as polyethylene or water irradiated with an electron beam normally incident to the product. The three curves represent different accelerator voltages for an electron beam source. The curves demonstrate that as the voltage of the beam increases, the maximum/minimum dose ratio can be reduced especially for thin products. The explanation for this behavior is that the entrance and exit ratios approach 1 at higher energy levels. In other words, the energy of the electrons exiting the product target is substantially equivalent to that of the entering electrons.

Figure 2:
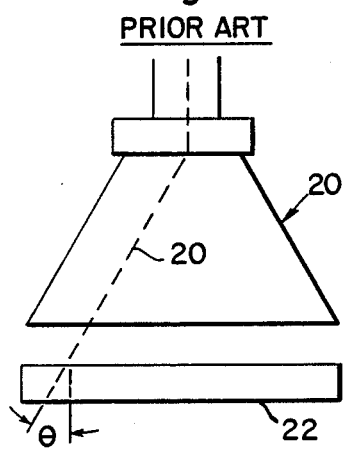
FIG. 2 schematically illustrates prior scanning horn and a target.

In FIG. 2, prior art scanner 20 irradiating product 22 is depicted. Beam 24 sweeps across product 22 at a preselected frequency. In FIG. 1 it is assumed that the beam entrance angle is normal to the product surface. It is clear, however, that the depth-dose distribution varies as the beam approaches the end of the scanner since the apparent thickness of the material increases. It should be readily appreciated that as the angle $\theta$ increases so does the amount of material the beam must penetrate This effective penetration depth is expressed by the simple geometric relationship; the product of dividing the target thickness by the cosine of angle $\theta$. This relationship clearly demonstrates the effective increase in product depth and corresponding reduction of dose density near the ends of the scan for relatively thicker products (beyond the maximum of the depth dose distribution curve). The adverse affect on dosage uniformity is not restricted to only this phenomena. The effective reduction is further exacerbated by the related reduction in effective secondary (scattered) electrons. Thus, the product edges corresponding to the end of the scan, in contrast to the center, not only present a significantly increased apparent thickness to the primary electrons but also the density of scattered electrons is significantly reduced.

Figure 3:
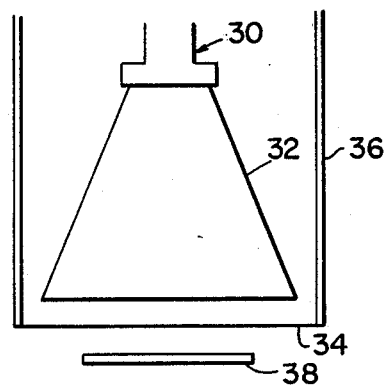
FIGS. 3 and 4 illustrate a scanning horn with variation of an intermediate scatter plate according to the invention.

Illustrated in FIG. 3 is an embodiment of the invention which is contemplated to assist in overcoming the non-uniformity dosage problem associated with a conventional source of 4.5 MeV high energy electrons 30. Beam source 30 includes scan horn 32 (with an electron permeable window, not illustrated) for directing the beam into target 38. Intermediate scatter plate 34, supported by elements 36, is positioned between horn 32 and target 38. For certain applications, it has been found that 4.5 MeV source 30 requires that scatter plate 34 have a thickness times density of approximately 0.1 to 0.3 gram per square centimeter (corresponding to approximately 5 to 15 mil stainless steel). In the case of non-uniform products, however, the specific configuration and density of the intermediate scatter plate may be tailored to the particular requirements by empirical testing (mathematical analysis is possible but expensive). Also of practical concern is the problem of overheating of the scatter plate during irradiation processing. As will become clear below several alternative concepts for overcoming this problem are suggested.

Figure 4:
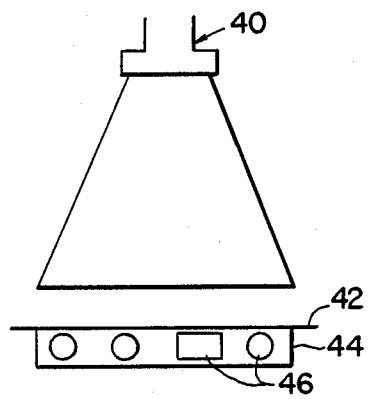
Figure 5:
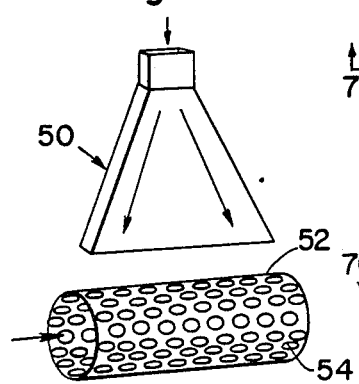
FIG. 5 is a perspective view of a perforated cylindrical intermediate energy modulator in accordance with this invention.

FIGS. 4 and 5 present variations of the configuration of the intermediate scatter plate. Intermediate scatter plate 42, in FIG. 4, is disposed between scanner 40 and box-like container 44 which supports non-uniform products 46. In FIG. 5, scanner 50 is associated with cylindrical dose attenuator 52. Attenuator 52 is perforated with apertures 54. To resolve the problem of scatter plate 52 overheating during scanning operations, air is blown at a reasonable high flow rate for cooling. In the illustrated embodiment, cylinder 52 is perforated to impart intermittent beam blockage (explained below) and may be rotated to enhance target dose uniformity. It should be readily apparent that as the beam scans and cylinder 52 is rotated, only certain portions of the cylinder are heated by electron bombardment. The bombardment zone is constantly changing due to the combined effect of the scanning and rotation.

Referring to dosage uniformity, the perforations modify a portion of the impinging radiation but permit a portion of the electron beam energy to pass unmodified. The modified portion will effectively increase the surface dose of the underlying target but the unmodified portion will permit maximum electron penetration. Since the unmodified beam energy is preferably selected to exhibit an equal entrance/exit ratio, the increased surface dosage can be compensated for by the penetration of the target with the electrons, which after passing through the target, are reflected by a back scatter plate (described below).

An additional delineated benefit of a perforated metal cylinder plate is convertibility. A series of interchangeable cylinders provide effective customization of the irradiation system. By merely changing the configuration, size, shape or quantity of plate holes or slots 54 in cylinder 52 (or plate), varying energy modification of the beam is achievable.

Figure 6:
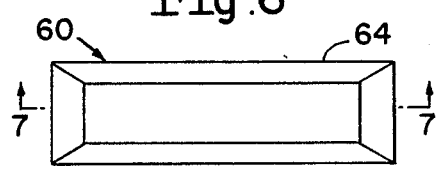
FIGS. 6 and 7 are, respectively, diagrammatic top and side views of an angled side scatter plate basket according to certain aspects of this invention.

As noted above, dosage uniformity in a target can be effectively increased by reflecting non-intersecting electrons into target edges. FIG. 6 depicts side scatter plate basket 60 which is intended to satisfy this purpose. Basket 60 employs angled wall 64 with bottom aperture 62. It is positioned peripheral to the target to ensure a reflection of electrons scattered from the product periphery. In essence, basket 60 provides alternative angular presentation of the scattered electrons to the target. Basket 60 should be composed of an intermediate or high density, high atomic number, i.e. steel, Tantalum, etc., material to maximize electron reflectivity and, thus, scattering back into the product. High density material also minimizes absorption of electrons in the scatter plate. 100 mil stainless steel has been found acceptable for construction of side scatter plates 60.

Figure 7:
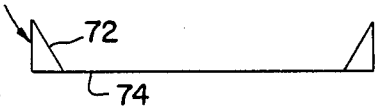

FIG. 7 illustrates another view of an alternative structure of the basket. Reflective box 70 incorporates angled side walls 72 and bottom scatter plate 74. The preferred range of angles for side wall 72 is 23 to 68 degrees and preferably, 45 degrees. As above, 100 mil or greater thickness steel is preferred for the construction of scatter box 70 to insure that both the primary and secondary electrons striking the side scatter plates or the bottom are reflected into the product to contribute to dose uniformity.

Figure 8:
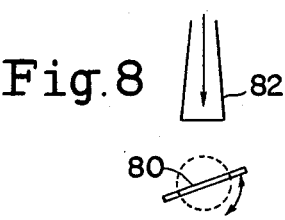
FIG. 8 is an end view of a rotatable intermediate plate in accordance with aspects of this invention.
Figure 9:
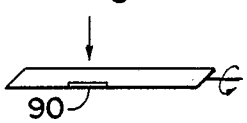
FIG. 9 is an elevational view of a rotating scatter plate which rotates in and out of the beam scan plane.

Referring briefly to FIG. 8, it diagrammatically represents a rotatable steel energy modification plate (scatter plate) which employs to its own advantage, the apparent thickness concept described above. In this case, intermediate steel (foil) plate 80 is rotatably mounted between horn 82 and the target (undesignated). It is preferred that the width of scatter plate 80 substantially exceed the beam path width of scanner horn 82 so as to permit effective attenuation. As plate 80 is rotated, the apparent thickness of the plate increases as the function of the cosine of the angle of rotation from a plane normal to the direction of scan. FIG. 9 represents a modification of that concept where plate 90 rotates in and out of the beam. In other words, the axis of rotation is located just outside and parallel to the beam scan plane.

Figure 10:
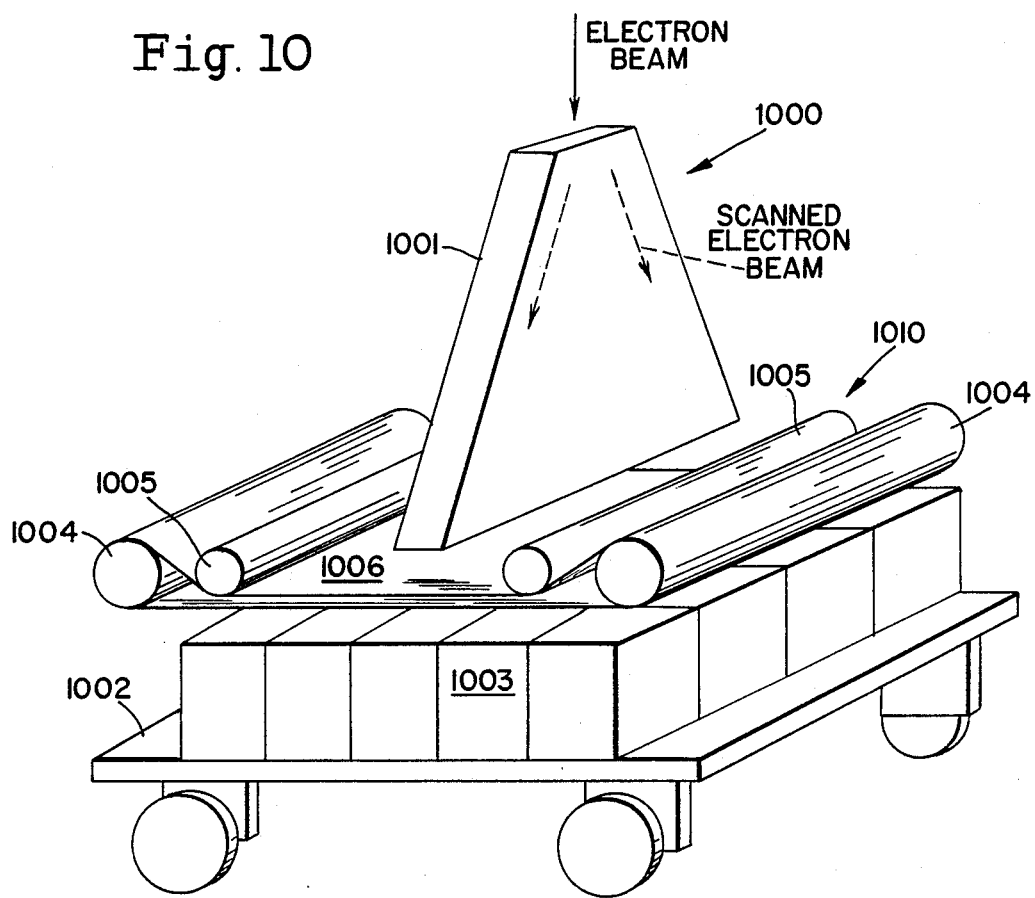
FIG. 10 is a perspective schematic view of a system embodiment in accordance with this invention.

Moving now to FIG. 10, it is illustrative of a system embodiment of the invention. System 1000 includes electron beam scanning horn 1001, cart 1002 capable of carrying product 1003 on a track (not illustrated). Energy modification module 1010 includes two remotely spaced, rotating, water cooled power drums 1004. Only one of drums 1004 need be connected to a rotating actuation means while the other is freely rotatable. Energy modifying endless metal foil belt 1006 (the scatter plate) is looped around drums 1004. Belt 1006 can be perforated for the reasons specified above. Guide rollers 1005 are disposed proximate to and parallel with drums 1004 to maintain control of the tension of belt 1006 while ensuring maximum surface engagement of belt 1006 on water cooled drum 1004. As belt 1006, resembling a conveyer, moves through the scanning beam and over drums 1004, it is alternately heated and cooled, respectively.

Figure 11:
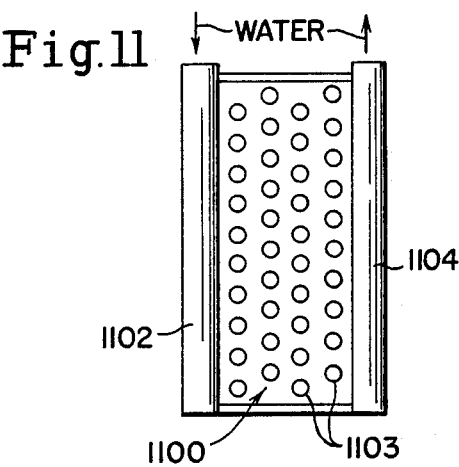
FIG. 11 is a top view of another embodiment of a modulator plate in accordance with this invention.
Figure 12:
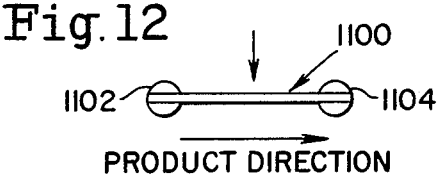
FIG. 12 is a side view of the embodiment of FIG. 11.

FIGS. 11 and 12 relate to yet another embodiment; water cooled, stationary, perforated, energy modulation plate 1100. Manifolds 1102 carry water pumped by any conventional means to and from plate 1100. Manifold tubes 1102 and 1104 may define connected input and output tubes or each may be a unidirectional pipe. In the former case, plate 1100, itself being formed from two spot-welded, matched metal foil layers enabling water communication therebetween, may provide an internal water passage between input tube 1102 and output tube 1104. In this event, plate 1100 can take advantage of the beam modifying properties of water (see FIG. 1). Water circulation therefore, cools the plate while contributing to its overall effectiveness.

Figure 13:
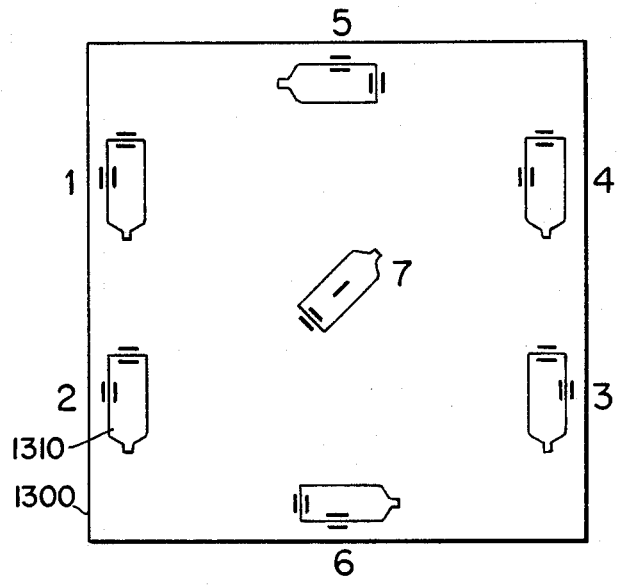
FIG. 13 is a top schematic view of targets on a carrier tray.

FIG. 13 is representative of a testing arrangement. More specifically, the test was conducted to demonstrate the various max/min doses of 8 oz. polyethylene bottles having a mass of approximately 25 to 30 grams each, irradiated in the configuration graphically represented in FIG. 13. Due to difficulties in achieving uniform dosage, generally experienced with such articles, a scatter basket of the type depicted in FIG. 7, was employed. Accordingly, the bottles were put into plastic bags and randomly placed in wire trays set within scatter baskets, which in turn, were set on a conveyer moving at a rate of 20 feet per minute. These were then exposed to a 4.5 MeV beam at 15 mA with and without attenuation scatter plates. Conventional dosimeters were placed on the bottles at specific location. The scatter plate and scatter basket were constructed from 10 mil stainless steel and 100 mil stainless steel sheeting, the side walls being disposed at a 45 degree angle, respectively.

The following observations were noted from the results obtained from the experiment:

1. The max/min dose ratio was reduced from 3.2 to 1.5.

2. Standard deviation was reduced from 0.77 Mrads to 0.29 Mrads.

3. Dosage spread was reduced from 3.4 Mrad to 1.2 Mrad.

Figure 14:
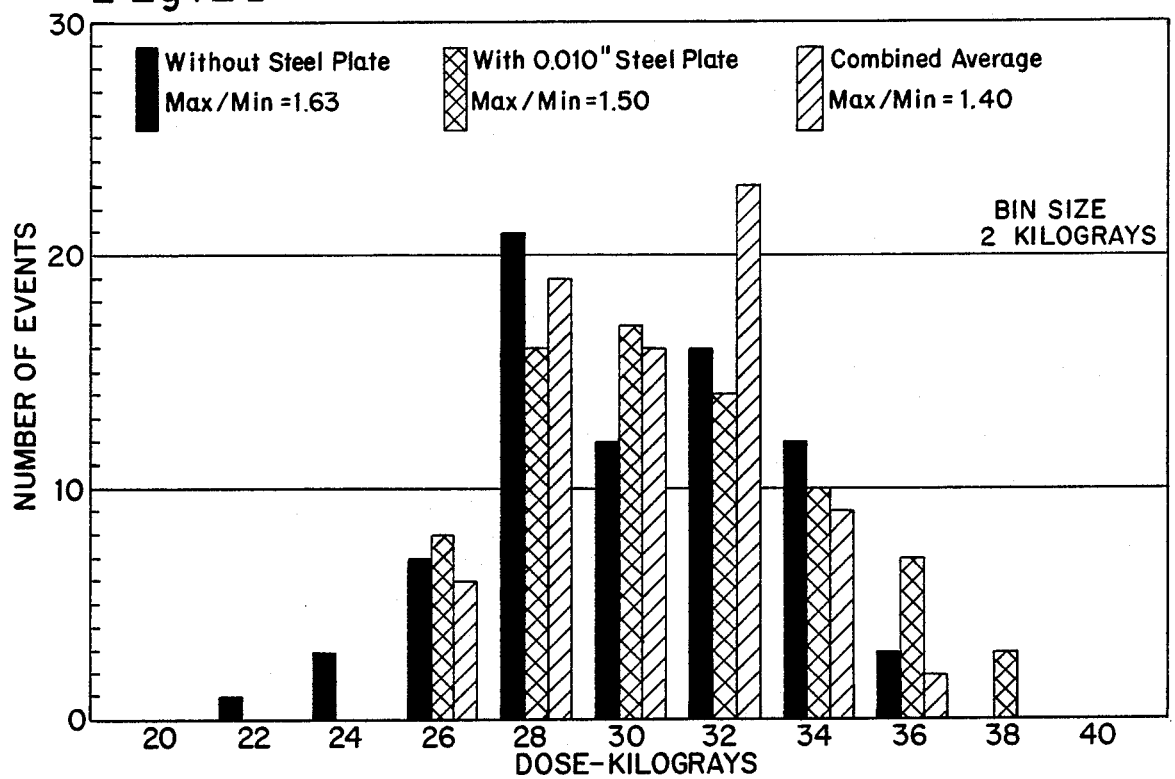
FIGS. 14, 15, 16 and 17 are histograms of comparative dosages using plates of different characteristics and differential exposure to the beam.
Figure 15:
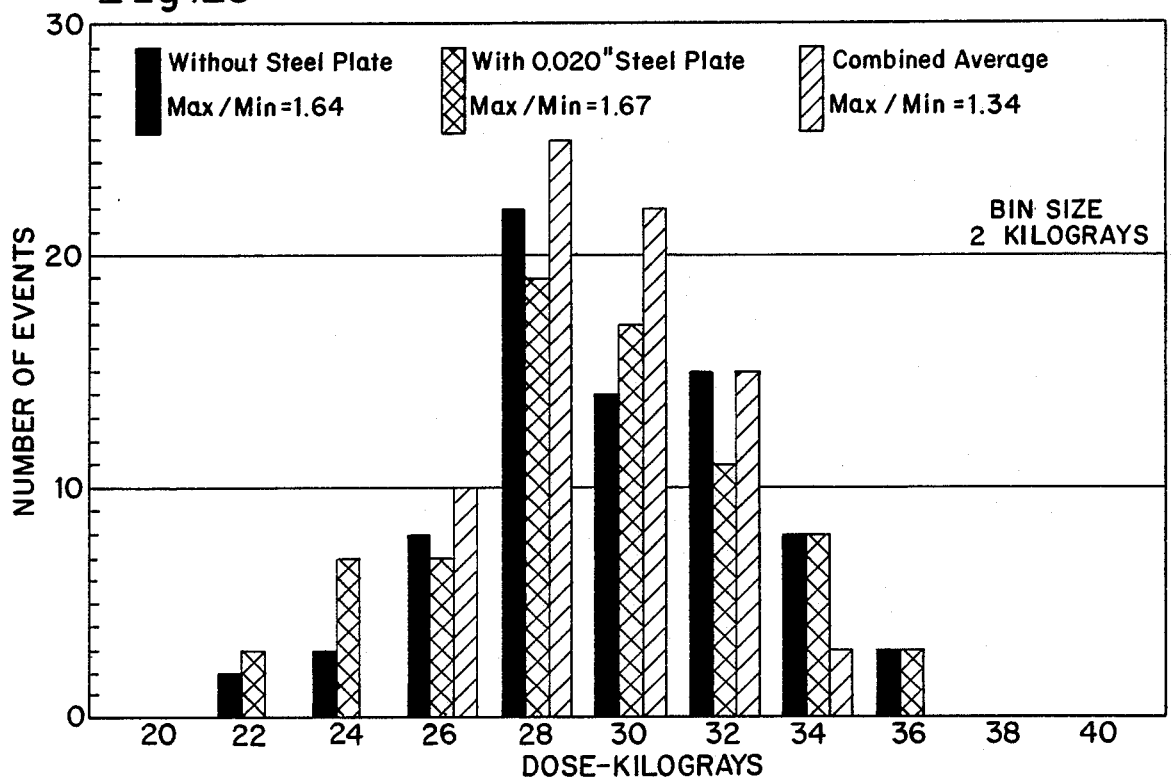

A second experiment, one directed to comparative analysis, was conducted employing 10 and 20 mil steel plates with an electron beam source having an energy greater 4.0 MeV. Cartons of syringes, tagged with dosimeters, were irradiated with and without the scatter plate. The combined average of the two scans was preferable. The histograms of FIGS. 14 and 15 indicate projected dose distribution with and without the respective energy modulation plates. The histograms represent graphically that min/max dose combined average was reduced with both the 10 and 20 mil plates. Furthermore, analysis of the results suggested that value obtained for the calculated respective dosage would be the same value obtained with a perforated steel plate having an open percentage of 50%.

Figure 16:
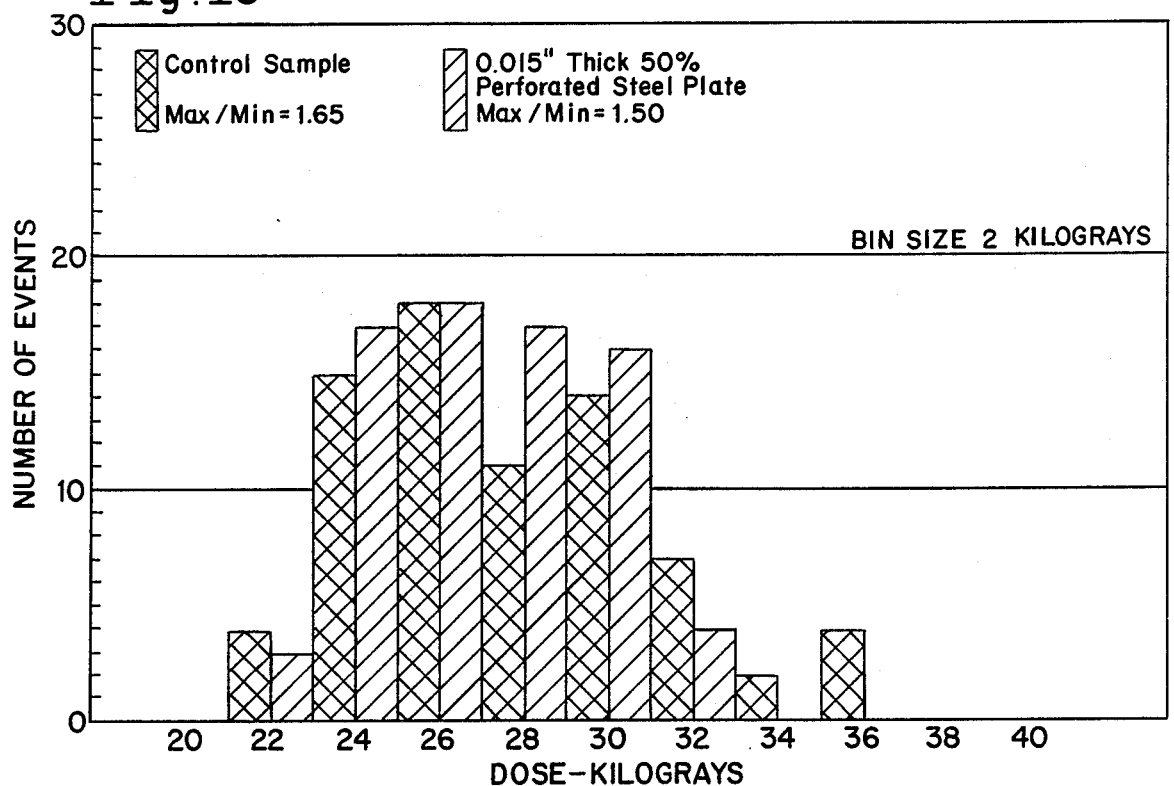
Figure 17:
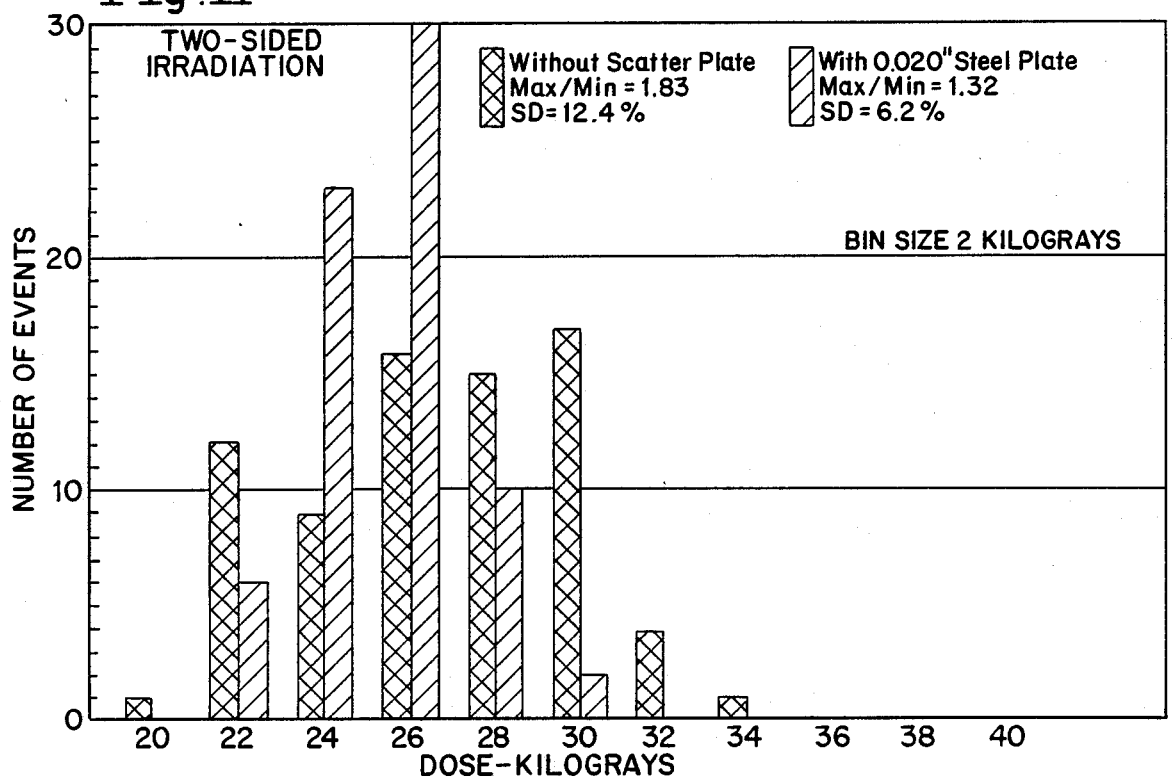

The histograms of FIGS. 16 and 17 were generated from the results of such testing. In reference to FIG. 16, targets were irradiated with a 15 mil (50%) perforated steel plate which was installed as part of the product carrier. While the results are not optimal, they demonstrate the anticipated beneficial characteristics of the invention. To improve the max/min ratio, the results suggest varying one or more of the parameters such as plate thickness, stationary positioning (see FIG. 11), etc.

In FIG. 17, the validity of combining the dose distributions is demonstrated. The test results which involved irradiating boxes of syringes with and without a 20 mil scatter plate, confirm the theory. The syringes were exposed two times each on both sides with and without the plate. Subsequently the radiation levels on the dosimeters were recorded. The results indicate the benefit of exposure to primary and secondary (ion scattered) electrons. In essence, the alternate exposure shifts the positions of maximum and minimum doses. Accordingly, the maximum and minimum doses of the combined treatment are less and more than either the individual maximum or minimum, respectively.

Given the foregoing, many variations, combinations and modifications of the instant invention should now be readily apparent to the person of ordinary skill in the art and, consequently, are intended to fall within the spirit and scope of the invention defined by the following claims.

We claim:

1. Apparatus for promoting radiation dose uniformity in exposed targets, comprising:
    a source of ionizing radiation, said source including means for generating a beam of ionizing radiation a scan zone and a beam exit window;
    target support means for supporting the targets, said target support means being located at a selected distance from said window;
    a rotatable mass means for absorbing energy of said radiation and inducing increased radiation scattering, said mass means being located between said window and said target support means; and
    cooling means for cooling said mass means.

2. Apparatus according to claim 1 where said ionizing radiation is a scanned high energy electron beam.

3. Apparatus according to claim 2 where said target support means includes an electron-reflective basket for directing scattered electrons into the target.

4. Apparatus according to claim 3 where said basket is composed of approximately 100 mil stainless steel plate and has a bottom and side walls disposed at an angle of 23-68 degrees relative to the direction of the beam.

5. Apparatus according to claim 2 where said mass means is a stainless steel plate.

6. Apparatus according to claim 5 where said plate is perforated.

7. Apparatus according to claim 5 further including oscillating operative means for oscillating said plate in and out of said beam.

8. Apparatus according to claim 1 where said mass means is an endless belt of metal foil and further comprising drive means for translating said belt through the scan zone.

9. Apparatus according to claim 8 where said foil is perforated.

10. A device for promoting uniform electron dosage in non-homogeneous products comprising:
    an electron beam source,
    means for producing a beam of adjustable energy;
    a target container for containing non-homogeneous products, said container including electron impermeable side scatter plates disposed at an angle sufficient to reflect scattered electrons impinging thereon toward the target container,
    a rotatable dose attenuator means for attenuating the beam energy and for inducing enhanced electron scatter, said attenuator means being of selected electron permeable thickness and positioned between said source and said container,
    bottom plate of high density material to enhance reflection of primary and secondary electrons toward the product, and
    cooling means for cooling said attenuator means.

11. A device according to claim 10 where said rotating attenuator means includes means for rotating said attenuator means in a plane normal to said beam whereby the apparent thickness of the attenuator means relative to the beam is adjusted by rotation thereof.

12. A device according to claim 11 where the angle of said side scatter plates is between 23-68 degrees relative to the direction of the electron beam.

13. A method of promoting dose uniformity in targets exposed to a beam of ionizing radiation issuing from an accelerator window, comprising the steps of:
    adjusting the irradiation energy level to achieve at least an equal entrance and exit dose level for the average thickness and density of the target;
    positioning a scatter plate between the target and the accelerator window to absorb a portion of the beam energy and to induce radiation scattering;
    increasing the apparent thickness of said plate relative to the beam by rotation of the plate; and
    cooling the scatter plate.

14. A method according to claim 13 further comprising the step of oscillating the scatter plate in and out of the beam.

15. A method, according to claim 13, where the scatter plate is metal foil.

16. A method according to claim 13 further including the step of perforating the scatter plate and moving the plate relative to the beam.

17. A method for attenuating the energy of a sweeping electron beam relative to a target, comprising the steps of:
    generating a sweeping electron beam of relatively high energy,
    inserting a rotatable, partially electron permeable metal element between the beam source and the target,
    modifying the beam energy,
    inducing increased electron scatter substantially by means of said metal element,
    positioning an electron reflective element around the target,
    directing scattered electrons from the reflective element into the target by means of said reflective element, and
    cooling the metal element.

18. The method according to claim 17 where the metal element is oscillated in and out of the beam.

* * * * *